United States Patent [19]

Bohni et al.

[11] 4,089,950
[45] May 16, 1978

[54] ANTIBACTERIAL COMPOSITIONS

[75] Inventors: Erika Bohni; Marc Montavon, both of Basel, Switzerland

[73] Assignee: Hoffmann-La Roche Inc., Nutley, N.J.

[21] Appl. No.: 794,422

[22] Filed: May 6, 1977

Related U.S. Application Data

[62] Division of Ser. No. 676,581, Apr. 13, 1976, Pat. No. 4,039,667, which is a division of Ser. No. 529,179, Dec. 3, 1974, Pat. No. 3,996,357.

[30] Foreign Application Priority Data

Dec. 12, 1973  Switzerland ............... 17400/73

[51] Int. Cl.$^2$ ................ A61K 31/625; A61K 31/505
[52] U.S. Cl. ................................. 424/229; 424/251
[58] Field of Search ........................ 424/229, 251

[56] References Cited

PUBLICATIONS

Roth et al., J. Med. Pharm. Chem. S, (1962), pp. 1103 and 1118–1121.
Chemical Abstracts, 69:69030f, (1968).
Chemical Abstracts, 78:132035k, (1973).
The Merck Index, 8th ed., 1968, Merck & Co., Inc., Rahway, N. J., p. 1077.

*Primary Examiner*—Jerome D. Goldberg
*Attorney, Agent, or Firm*—Samuel L. Welt; George M. Gould; William G. Isgro

[57] ABSTRACT

Compositions comprising N-sulfanilyl-1-ethylcytosine and a sulfonamide potentiator, which are useful as antibacterial agents, are described.

4 Claims, No Drawings

ANTIBACTERIAL COMPOSITIONS

CROSS-REFERENCE TO RELATED APPLICATIONS

This is a division, of application Ser. No. 676,581 filed Apr. 13, 1976, now U.S. Pat. No. 4,039,667, issued Aug. 2, 1977, which in turn is a division of U.S. Pat. application Ser. No. 529,179, filed Dec. 3, 1974, now U.S. Pat. 3,996,357, issued Dec. 7, 1976.

BRIEF SUMMARY OF THE INVENTION

The invention relates to antibacterial compositions comprising N-sulfanilyl-1-ethylcytosine, which has the formula

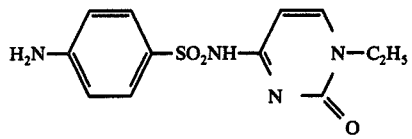

I or a pharmaceutically acceptable salt thereof with a strong base and a sulfonamide potentiator, for example, a 2,4-diamino-5-benzylpyrimidine potentiator.

DETAILED DESCRIPTION OF THE INVENTION

The antibacterial compositions of the invention contain the sulfonamide of the formula

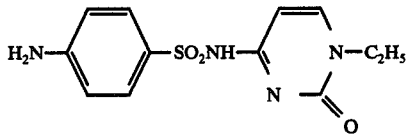

I or a pharmaceutically acceptable salt thereof with a strong base and a sulfonamide potentiator.

The compound of formula I is a known compound and has antibacterial activity. Unexpectedly, it has been found that by the addition of a sulfonamide potentiator, the chemotherapeutic activity of the compound of formula I and its salts, especially the antibacterial activity in urine, can be surprisingly increased to a significant extent.

Particularly suitable sulfonamide potentiators in accordance with the invention are 2,4-diamino-5-benzyl-pyrimidines of the formula

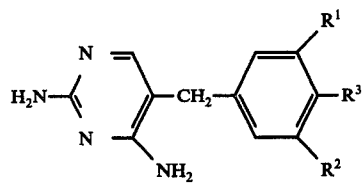

II wherein $R^1$ is lower alkoxy, $R^2$ is lower alkoxy and $R^3$ is amino, (lower alkyl)amino, di(lower alkyl)amino or lower alkoxy,
or pharmaceutically acceptable acid addition salts thereof.

As used herein, the terms "lower alkyl" and "lower alkoxy" denote straight-chain and branched-chain alkyl and alkoxy, respectively, which preferably contain from 1 to 7 carbon atoms, most preferably, from 1 to 4 carbon atoms, such as methyl, methoxy, ethyl, ethoxy, propyl, propoxy, isopropyl, isopropoxy, butyl, isobutyl, tert.-butyl, isobutoxy, tert.-butoxy or the like. A preferred lower alkoxy is methoxy. Particularly preferred 2,4-diamino-5-benzyl-pyrimidines of formula II are 2,4-diamino-5-(3,4,5-trimethoxybenzyl)-pyrimidine and 2,4-diamino-5-(4-amino-3,5-dimethoxybenzyl)-pyrimidine.

The 2,4-diamino-5-benzyl-pyrimidines of formula II, insofar as they are not known, can be prepared either in a known manner or, for example, by chlorinating or brominating a compound of the formula

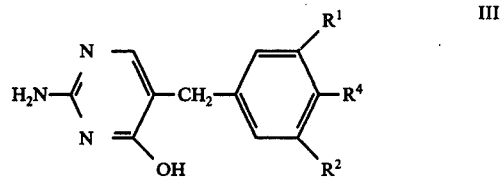

III wherein $R^4$ is amino, (lower alkyl)amino or di(lower alkyl)-amino and $R^1$ and $R^2$ are as previously described, in a known manner and reacting the resulting halo compound with ammonia. The reaction with ammonia is conveniently carried out in alkanolic, preferably methanolic solution, at a temperature in the range of from about 80° C. to about 200° C., preferably in the range of from about 100° C. to about 150° C. Since these temperatures are above the boiling point of methanol, the reaction is carried out in a closed system, for example, in an autoclave.

Physiologically and pharmaceutically acceptable acid addition salts of 2,4-diamino-5-benzyl-pyrimidines of formula II can be prepared using conventional inorganic and organic acids, such as hydrochloric acid, sulfuric acid, phosphoric acid, formic acid, acetic acid, malonic acid, succinic acid, malic acid, citric acid, tataric acid, maleic acid, fumaric acid, methanesulfonic acid, p-toluene-sulfonic acid or the like.

As physiologically or pharmaceutically acceptable strong bases for the preparation of salts of N-sulfanilyl-1-ethylcytosine of formula I there can be used conventional inorganic and organic bases, for example, alkali metal hydroxides and alkanolamines such as ethanolamine, and the like.

The weight ratio of sulfonamide to sulfonamide potentiator in the antibacterial compositions provided by the invention conveniently is in the range of from about 1:1 to about 40:1, preferably 5:1. The antibacterial compositions of the invention include not only mixtures which consist solely of the two active ingredients, namely, the sulfonamide and the sulfonamide potentiator, but also mixtures which contain one or more additional substances, for example, active ingredients.

The process provided by the invention for the preparation of the antibacterial compositions comprises mixing the sulfonamide of formula I with the sulfonamide potentiator ingredient. The sulfonamide and the sulfonamide potentiator is conveniently used in a weight ratio of from about 1:1 to about 40:1, preferably 5:1. The process can be carried out in a known manner.

The antibacterial compositions provided by the invention, which possess good tolerance or slight or low toxicity, are active against gram-positive and gram-negative bacteria, such as coli and Proteus bacilli, Klebsiellae, Aerobacter, Entercocci, or the like. The antibacterial compositions are particularly active, for example, against Escherichia coli, Proteus vulgaris, Proteus mirabilis, Klebsiella pneumoniae, Aerobacter aerogenes and Streptococcus faecalis. Accordingly, the compositions of the invention are suitable for combating and preventing bacterial infections, especially the so-called cavity infections, such as infections of the urinary tract. The antibacterial compositions of the invention can be administered orally or parenterally.

When 200 mg/kg. of a 5:1 mixture of N-sulfanilyl-1-ethylcytosine and 2,4-diamino-5-(3,4,5-trimethoxybenzyl)-pyrimidine were administered orally to rats a very high order of activity was observed. The activity, measured in urine, of this combination against E. coli is, for example, 92 times greater than that of 200 mg/kg. of N-(5-nitro-2-furfuryliden)-1-amino-hydantoin and 203 times greater than that of the corresponding amount (namely 167 mg/kg.) of the unpotentiated N-sulfanilyl-1-ethylcytosine.

The antibacterial compositions provided by the invention can be administered in the form of pharmaceutical preparations which contain an organic or inorganic, inert carrier material suitable for oral or parenteral administration, for example, water, gelatin, gum arabic, lactose, starch, magnesium stearate, talc, vegetable oils, polyalkyleneglycols, or the like. The pharmaceutical preparations can be made up in a solid form, for example, as tablets, dragees, suppositories or capsules, or in a liquid form, for example, as solutions, suspensions or emulsions. The compositions may be sterilized and/or may contain adjuvants such as preservatives, stabilizers, wetting agents, emulsifiers, salts for varying the osmotic pressure or buffers.

The preparation of the pharmaceutical preparations can be carried out in a known manner.

A suitable tablet can, for example, contain 400 mg. of N-sulfanilyl-1-ethylcytosine and 80 mg. of 2,4-diamino-5-(3,4,5-trimethoxybenzyl)pyrimidine or it can, for example, contain 50% of each of these amounts. The dose administered daily can be, or has to be, suited to individual requirements and can be varied within wide limits.

The following Examples further illustrate the invention.

EXAMPLE 1

Medicinal preparations containing N-sulfanilyl-1-ethylcytosine and 2,4-diamino-5-(3,4,5-trimethoxybenzyl)-pyrimidine in a weight ratio of 5:1 (active ingredient) can comprise the following:

(a) Tablets:

|  | Formulation A | Formulaton B |
|---|---|---|
| N-sulfanilyl-1-ethylcytosine | 400 mg. | 200 mg. |
| 2,4-diamino-5-(3,4,5-trimethoxybenzyl)pyrimidine | 80 mg. | 40 mg. |
| Mannitol | — | 50 mg. |
| Lactose | 30 mg. | 50 mg. |
| Microcrystalline cellulose | 120 mg. | 147 mg. |
| Tylose | 5 mg. | 3 mg. |
| Talc | 14 mg. | 9 mg. |
| Magnesium stearate | 1 mg. | 1 mg. |
|  | 650 mg. | 500 mg. |

The active ingredients are mixed with a portion of the microcrystalline cellulose, lactose and, optionally, maize starch. The mixture is granulated with an aqueous or alcoholic/aqueous Tylose solution and dried and, after the addition of the remaining ingredients, pressed into tablets.

(b) Injection solution in 5 ml. ampules:

|  | Formulation A | Formulation B |
|---|---|---|
| N-sulfanilyl-1-ethylcytosine | 400.0 mg. | 400.0 mg. |
| 2,4-diamino-5-(3,4,5-trimethoxybenzyl)-pyrimidine | 80.0 mg. | 80.0 mg. |
| Sodium hydroxide | 59.1 mg. | — |
| Diethanolamine | — | 155.4 mg. |
| Water for injection purposes ad 5 ml. |  |  |

The ampules are filled under nitrogen and sterilized in an autoclave at 120° C.

(c) Capsules:

|  | Formulation A | Formulation B |
|---|---|---|
| N-sulfanilyl-1-ethylcytosine | 200.0 mg. | 400.0 mg. |
| 2,4-diamino-5-(3,4,5-trimethoxybenzyl)-pyrimidine | 40.0 mg. | 80.0 mg. |
| Methylcellulose | 2.5 mg. | 5 mg. |
| Talc | 4.0 mg. | 8 mg. |
| Modified starch | 7.5 mg. | 15 mg. |
| Magnesium stearate | 1.0 mg. | mg. |
|  | 255.0 mg. | 510 mg. |

The active ingredients are moistened with a methylcellulose solution and kneaded. The mass is then granulated, dried and sieved. A mixture of the modified starch, talc and magnesium stearate is mixed with the granulate. Filling into interlocking gelatin capsules is carried out on an automatic capsule filling machine.

EXAMPLE 2

Medicinal preparations containing N-sulfanilyl-1-ethylcytosine and 2,4-diamino-5-(4-amino-3,5-dimethoxybenzyl)-pyrimidine in a weight ratio of 5:1 (active ingredient) can comprise the following:

(a) Tablets

|  | Formulation A | | Formulation B | |
|---|---|---|---|---|
| N-sulfanilyl-1-ethyl-cytosine | 416.67 | mg. | 208.33 | mg. |
| 2,4-diamino-5-(4-amino-3,5-dimethoxybenzyl)-pyrimidine | 83.33 | mg. | 41.67 | mg. |
| Mannitol | 30 | mg. | 30 | mg. |
| Maize starch | 50 | mg. | 30 | mg. |
| Talc | 18 | mg. | 9 | mg. |
| Magnesium stearate | 2 | mg. | 1 | mg. |
|  | 600 | mg. | 320 | mg. |

The active ingredients are mixed with the mannitol and a portion of the maize starch, moistened with a maize starch paste and kneaded. The mass is then granulated, dried and sieved and, after the addition of the remaining ingredients, can be pressed into tablets.

(b) Capsules:

|  | Formulation A | | Formulation B | |
|---|---|---|---|---|
| N-sulfanilyl-1-ethyl-cytosine | 416.67 | mg. | 208.33 | mg. |
| 2,4-diamino-5-(4-amino-3,5-dimethoxybenzyl)-pyrimidine | 83.33 | mg. | 41.67 | mg. |
| Hydroxypropyl methylcellulose | 5 | mg. | 3 | mg. |
| Modified starch | 10 | mg. | 7 | mg. |
| Talc | 9 | mg. | 9 | mg. |
| Magnesium stearate | 1 | mg. | 1 | mg. |
|  | 525 | mg. | 270 | mg. |

The active ingredient is moistened with an aqueous hydroxypropyl methylcellulose solution and kneaded. The mass is then granulated, dried and sieved and, after the addition of the remaining ingredients, is ready for filling into capsules on an automatic capsule filling machine.

We claim:

1. An antibacterial composition comprising the sulfonamide of the formula

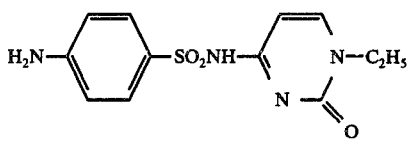

or a pharmaceutically acceptable salt thereof with a strong base and a sulfonamide potentiator of the formula

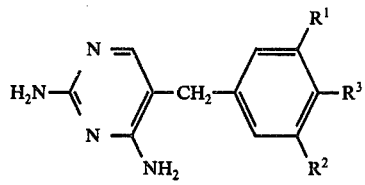

wherein $R^1$ and $R^2$ are lower alkoxy and $R^3$ is (lower alkyl)-amino or di(lower alkyl)amino, or a pharmaceutically acceptable acid addition salt thereof, wherein the weight ratio of sulfonamide to sulfonamide potentiator is in the range of from 1:1 to 40:1.

2. A composition in accordance with claim 1, wherein the weight ratio of sulfonamide to sulfonamide potentiator is 5:1.

3. A composition in accordance with claim 1, wherein the sulfonamide potentiator is 2,4-diamino-5-[4-(dimethylamino)-3,5-dimethoxybenzyl]pyrimidine.

4. A composition in accordance with claim 1, wherein the sulfonamide potentiator is 2,4-diamino-5-[4-(ethylamino)-3,5-dimethoxybenzyl]pyrimidine.

* * * * *